(12) United States Patent
Zhai et al.

(10) Patent No.: US 8,754,273 B2
(45) Date of Patent: *Jun. 17, 2014

(54) PROCESS FOR PREPARING 1,1,2-TRICHLORO-3,3,3-TRIFLUOROPROPANE

(71) Applicant: Honeywell International Inc., Morristown, NJ (US)

(72) Inventors: Yian Zhai, Amherst, NY (US); Andrew Joseph Poss, Kenmore, NY (US); Rajiv Ratna Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,160

(22) Filed: Nov. 12, 2012

(65) Prior Publication Data

US 2013/0150634 A1    Jun. 13, 2013

Related U.S. Application Data

(60) Provisional application No. 61/567,679, filed on Dec. 7, 2011.

(51) Int. Cl.
| | | |
|---|---|---|
| *C07C 17/20* | (2006.01) | |
| *C07C 19/01* | (2006.01) | |
| *C07C 19/10* | (2006.01) | |
| *C07C 17/04* | (2006.01) | |

(52) U.S. Cl.
CPC ............... *C07C 17/206* (2013.01); *C07C 17/20* (2013.01); *C07C 19/01* (2013.01); *C07C 19/10* (2013.01); *C07C 17/04* (2013.01)
USPC .......................................... 570/170; 570/246

(58) Field of Classification Search
USPC .......................................................... 570/170
See application file for complete search history.

(56) References Cited

U.S. PATENT DOCUMENTS

| | | |
|---|---|---|
| 5,057,634 A | 10/1991 | Webster et al. |
| 5,714,655 A | 2/1998 | Yamamoto et al. |
| 7,067,705 B2 * | 6/2006 | Moscoe ........................ 570/101 |

FOREIGN PATENT DOCUMENTS

| | | |
|---|---|---|
| EP | 0729932 A1 | 9/1996 |
| WO | 9504022 A1 | 2/1995 |
| WO | 9943635 A1 | 9/1999 |
| WO | WO 2010029419 A1 * | 3/2010 |
| WO | WO 2010071136 A1 * | 6/2010 |

OTHER PUBLICATIONS

Kawaguchi, S. et al. Patent No. WO2010071136A1, English translation.*
Pigamo, A. et al. Patent No. WO2010029419A1, English translation.*
J. Am. Chem. Soc., 64 (1942) 1157-9.
PCT ISR & Written Opinion issued in PCT/US2012/066803 dated Mar. 18, 2013.

* cited by examiner

*Primary Examiner* — Fereydoun G Sajjadi
*Assistant Examiner* — Medhanit Bahta
(74) *Attorney, Agent, or Firm* — Erika S. Wilson

(57) ABSTRACT

Disclosed is a process for making the compound 1,1,2-trichloro-3,3,3-trifluoropropane (233da) by the catalytic fluorination of 1,1,1,2,3,3-hexachloropropane. 233da is a starting material used in the production cis-1-chloro-3,3,3-trifluoropropene (cis-1233zd).

5 Claims, No Drawings

PROCESS FOR PREPARING 1,1,2-TRICHLORO-3,3,3-TRIFLUOROPROPANE

CROSS-REFERENCE TO RELATED APPLICATION

This application claims domestic priority to commonly owned, copending U.S. Provisional Patent Application Ser. No. 61/567,679, filed Dec. 7, 2011, the disclosure of which is hereby incorporated herein by reference.

FIELD OF THE INVENTION

Disclosed is a process for making the compound 1,1,2-trichloro-3,3,3-trifluoropropane (HCFC-233da or 233da). The compound 233da is a starting material used in the production cis-1-chloro-3,3,3-trifluoropropene (cis-1233zd).

BACKGROUND OF THE INVENTION

This invention provides a starting material useful for the preparation of a hydrochlorofluoroolefin (HCFO) compound (cis-1233zd) which has negligible ozone depletion potential (ODP) and low global warming potential (GWP) and is suitable for use in applications such as blowing agents, solvents, and the like.

As described above, this invention is directed to processes for the formation of 233da, a compound used in the production of cis-1-chloro-3,3,3-trifluoropropene, which may be designated as HCFO-1233zd (Z), 1233zd (Z), or cis-1233zd. The compound 1233zd (Z) is a low global warming compound that has applications as a replacement for high global warming materials, for example in foam blowing and aerosol propellant applications.

Processes for converting halogenated hydrocarbons with HF into fluorine substituted species are known. The reactivities of different halogenated groups such as $CX_3$, $CHX_2$, $CH_2X$ (X=Cl, Br, I) are different toward the HF/metal halides under certain conditions. By choosing an appropriate metal catalyst and reaction temperature, the group $CX_3$ can be transferred into $CF_3$ group without affecting the other halogenated groups in the same molecule.

The compound 233da can be prepared by the following sequence of reactions;
 (a) chlorination of 1,1,1-trifluoropropane to yield 1,1,1-trifluoro-3,3-dichloropropane;
 (b) dehydrochlorination of 1,1,1-trifluoro-3,3-dichloropropane to yield 1233zd; and
 (c) chlorination of 1233zd to produce 233da.
See, J. Am. Chem. Soc., 64: 1157 (1942), the disclosure of which is hereby incorporated herein by reference.

SUMMARY OF THE INVENTION

This invention relates to the preparation of 233da which can be used as a precursor or starting material for the preparation of 1-chloro-3,3,3-trifluoropropene (1223zd).

One embodiment of this invention is directed to a process that generates 233da directly from a halogenated propane by fluorination, such as the fluorination of 1,1,1,2,3,3-hexachloropropane. This process yields a mixture of compounds which includes the desired product 233da.

Halogenated propane compounds can be fluorinated with HF using metal catalysts such as $SbCl_5$, $TiCl_4$, $SnCl_4$, $TaCl_5$, and $NbCl_5$ under variable temperatures.

In a typical reaction, a metal catalyst is treated with anhydrous HF first in a Monel autoclave at 70° C. to 90° C. until no further pressure increase is detected. Then, additional HF is charged into the autoclave followed by 1,1,1,2,3,3-hexachloropropane. The autoclave is sealed and heated to the desired reaction temperature, and held at that temperature for a certain amount of time. After work-up, the crude material is checked by GC and/or NMR and the desired compound 233da is isolated from the resulting mixture of reaction products.

One embodiment of the invention is directed to a process for making the compound 1,1,2-trichloro-3,3,3-trifluoropropane (233da) from 1,1,1,2,3,3-hexachloropropane comprising the steps:
 (a) fluorinating a metal catalyst; and
 (b) fluorinating 1,1,1,2,3,3-hexachloropropane in the presence of the fluorinated metal catalyst, to produce a reaction mixture containing 1,1,2-trichloro-3,3,3-trifluoropropane (233da).

In certain embodiments of this process, the metal catalyst is selected from the group consisting of $SbCl_5$, $TiCl_4$, $SnCl_4$, $TaCl_5$, $NbCl_5$, and the like. One preferred catalyst comprises $SbCl_5$. Another preferred catalyst comprises $TaCl_5$.

In certain embodiments, the fluorination of the catalyst is conducted at a temperature of about 90° C. for about two hours. In certain embodiments, the fluorination of the catalyst is conducted at a temperature of about 70° C. for about two hours.

In certain embodiments, the fluorination of the hexachloropropane is conducted at a temperature of about 100° C. for about 15 hours. In certain embodiments, the fluorination of the hexachloropropane is conducted at a temperature of about 100° C. for about 20 hours. In certain embodiments, the fluorination of the hexachloropropane is conducted at a temperature of about 90° C. for about six hours.

Another embodiment of the invention is directed to a process for making the compound 1,1,2-trichloro-3,3,3-trifluoropropane (233da) from trans-1-chloro-3,3,3-trifluoropropene (trans-1233zd) comprising reacting chlorine gas with trans-1233zd. In certain embodiments, this process is conducted at a reaction temperature of about 0° C.

DETAILED DESCRIPTION OF THE INVENTION

As described above, the present invention provides a process for the manufacture of the compound 233da. This compound can be produced in a number of ways such as the fluorination of chlorinated propanes, and by the chlorination of trans-1233zd.

Formation of 233da

In a typical reaction, metal catalyst is treated with anhydrous HF first in Monel autoclave at from about 70° C. to 90° C. until no pressure increase is noted. Then, the formed HCl gas is removed and additional HF is charged into the autoclave followed by 1,1,1,2,3,3-hexachloropropane. The autoclave is sealed again and heated to the desired temperature for certain amount of time. After work-up, the reaction mixture containing 233da is checked by GC and NMR for product distribution.

Formation of 1233zd

In a typical dehalogenation reaction, zinc, solvent, and catalyst are mixed and heated to within a few degrees of the reaction temperature, typically between 50° C. and 150° C., preferably between 70° C. and 100° C. HCFC-233da is then added over time to control the reaction, as the production of 1233zd is exothermic. The temperature of the reaction mixture may initially increase from about 5° C. to 10° C. and then the reaction temperature is allowed to return to the original reaction temperature before another portion of 233da is added.

Alternatively, 233da may be added mechanically at a set rate that is slow enough to maintain the desired reaction temperature. After the addition is complete heating is continued for a time to ensure that all the 233da has reacted. Generally, it is advantageous to remove 1233zd as it is formed, but this is not required.

Example 1

To 15.5 g of $SbCl_5$ in 450 mL Monel autoclave was added 18.0 g of anhydrous HF under a nitrogen atmosphere and the autoclave reactor was heated to 90° C. for 2 hours. The pressure stopped increasing (at 400 psig) and thereafter the reactor was cooled to 0° C. and vented under nitrogen atmosphere through a basic scrubber. Another 40.0 g of HF was charged into the autoclave at −78° C. followed by 30.0 g of 1,1,1,2,3,3-hexachloropropane.

The autoclave was sealed and the reaction mixture was heated to 100° C. for 15 hours, at a pressure of 400 psig. The mixture was cooled to 0° C. and the reactor was vented through a basic scrubber solution.

The liquid inside the autoclave was diluted with 40 mL of DI water and separated from the separator funnel. The organic layer was washed with DI water twice then diluted with a 10% $NaHCO_3$ solution. 9.5 g of brown liquid was collected, which contained 38.6% of 233da, with a mixture of dichloro-trifluoro propene isomers, cis-1223xd (52.2%) and trans-1223xd (9.2%), as determined by NMR analysis.

Example 2

A 450 mL Monel autoclave was charged with 10 mL of 1,3-bis(trifluoromethyl)-benzene and 5.5 g of $SbCl_5$ under nitrogen. The autoclave was sealed and cooled to −78° C. and then charged with 15.0 g anhydrous HF. The mixture was then heated to 70° C. for 2 hours until no further pressure increase (above 400 psig) was noted.

The mixture was vented under nitrogen at 0° C.; next the system was cooled to −78° C. with dry-ice and charged with 60.0 g HF and 30.0 g 1,1,1,2,3,3-hexachloropropane, sealed and heated to 100° C. for 20 hours, at a pressure of 400 psig. The mixture was cooled to 0° C. and vented through basic scrubber.

The liquid inside the autoclave was washed with DI water three times followed by diluted (10%) $NaHCO_3$ solution. The mixture contained 35.5% of 233da, 1223xd isomers (53.2%), and $CF_2ClCHClCHCl_2$ (11.3%), as determined by NMR analysis.

Example 3

A 450 mL Monel autoclave reactor was charged with 8.6 g of $TaCl_5$ under nitrogen. The autoclave was sealed and cooled to −78° C. and charged with 13.0 g anhydrous HF. The mixture was then heated to 90° C. for 2 hours until no further pressure increase (above 400 psig) was noted.

The mixture was vented under nitrogen at 0° C., then the system was cooled to −78° C. with dry-ice and charged with 30.0 g HF and 30.0 g 1,1,1,2,3,3-hexachloropropane, sealed and heated to 90° C. for 6 hours, at a pressure of 300 psig. The mixture was cooled to 0° C. and vented through basic scrubber.

The liquid inside the autoclave was washed with DI water three times followed by diluted (10%) $NaHCO_3$ solution. The mixture contained 5.1% of 233da, 1223xd isomers (54.4%), and $CF_2ClCHClCHCl_2$ (15.2%), plus some unidentified peaks, as determined by GC analysis.

Example 4

Chlorine gas (625 g, 8.80 mol) was bubbled into trans-1233zd (959 g, 7.34 mol) at 0° C. with a dry-ice acetone trap to recover the 1233zd vapor. The reaction progress was monitored by GC until the complete conversion of the starting material (trans-1233zd); the excess chlorine was washed away with sodium sulfite solution then water (1 time) after completion. The crude 233da (1462 g, 98.8% yield) obtained was essentially pure (99.6% pure).

Example 5

In a manner as described in Example 4, chlorine gas (650 g, 9.15 mol) was bubbled into the trans-1233zd (1011 g, 7.75 mol) at 0° C. The product 233da was formed, yielding 1525 g, 97.8% yield, at 99.0% pure.

Example 6

Preparation of 1233zd from 233da

The vessel for this reaction is essentially a distillation set-up, consisting of a four-necked 3000 mL flask fitted with an addition funnel, thermometer, mechanic stirrer and 2-foot reflux condenser controlled at 36° C. to 41° C. connected a distillation take-off adapter then to dry-ice acetone trap. Distillate and any material which passed by the condenser was collected in a cold trap at less than −50° C. The 233da used in herein was at least 99% pure.

The flask was charged with 2000 mL DI water, 20 mL of conc. HCl, and 428 g zinc dust. A total of 652 g, 3.23 mol of 233da was added over 4 to 5 h, starting at 55° C. and increasing to 80° C. to 82° C. after addition is complete. The reaction temperature was at 80° C. to 82° C. for 30 to 45 min. The cold trap contained 362.0 g liquid (85.8% yield), which analyzed as 51.8% of trans-1233zd and 42.4% of cis-1233zd, 1.2% of $CF_3CCl=CHCl$ (1223xd), and 4.3% of unreacted 233da.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A process for making the compound 1,1,2-trichloro-3,3,3-trifluoropropane (233da) from 1,1,1,2,3,3-hexachloropropane comprising the steps:

(a) fluorinating a metal catalyst consisting of SbCl$_5$; and
(b) fluorinating 1,1,1,2,3,3-hexachloropropane in the presence of the fluorinated metal catalyst at a reaction temperature in the range of 90° C. to 100° C. for a time period in the range of 6 to 20 hours, to produce a reaction mixture containing up to about 35% by weight of 1,1,2-trichloro-3,3,3-trifluoropropane.

2. The process of claim 1, wherein the fluorination of the catalyst is conducted at a temperature of about 90° C. for about two hours.

3. The process of claim 2, wherein the fluorination of the hexachloropropane is conducted at a temperature of about 100° C. for about 15 hours.

4. The process of claim 1, wherein the fluorination of the catalyst is conducted at a temperature of about 70° C. for about two hours.

5. The process of claim 4, wherein the fluorination of the hexachloropropane is conducted at a temperature of about 100° C. for about 20 hours.

\* \* \* \* \*